US005665368A

United States Patent [19]

[11] Patent Number: 5,665,368

[45] Date of Patent: Sep. 9, 1997

Lentini et al.

[54] SPRAYABLE COMPOSITIONS CONTAINING DISPERSED POWDERS AND METHODS FOR USING THE SAME

[75] Inventors: Peter J. Lentini, Glen Oaks; Paul C. Tchinnis, Copiague, both of N.Y.

[73] Assignee: Estee Lauder, Inc., New York, N.Y.

[21] Appl. No.: 753,031

[22] Filed: Nov. 19, 1996

Related U.S. Application Data

[63] Continuation of Ser. No. 333,707, Nov. 3, 1994, abandoned.

[51] Int. Cl.$^6$ .............................. A61K 6/00; A61K 7/11

[52] U.S. Cl. .............................. 424/401; 424/59; 424/709; 424/70.11; 424/70.12; 424/678; 424/680; 424/681; 424/682; 424/DIG. 2

[58] Field of Search .............................. 424/401, 59, 70.11, 424/70.12, 70.9, 678, 680–82, 709, DIG. 2

[56] References Cited

U.S. PATENT DOCUMENTS

| | | | |
|---|---|---|---|
| 4,350,605 | 9/1982 | Hughett | 424/47 |
| 4,897,262 | 1/1990 | Nandagiri et al. | 424/70.12 |
| 4,961,921 | 10/1990 | Chuang et al. | 424/70.12 |
| 4,983,377 | 1/1991 | Murphy et al. | 424/47 |
| 4,983,383 | 1/1991 | Maksmoski | 424/70.12 |
| 5,015,469 | 5/1991 | Yoneyama et al. | 424/59 |
| 5,066,485 | 11/1991 | Brieva et al. | 424/63 |
| 5,143,722 | 9/1992 | Hollenberg et al. | 424/63 |
| 5,164,177 | 11/1992 | Bhatt et al. | 424/70.16 |
| 5,196,187 | 3/1993 | Nicoll et al. | 424/70 |
| 5,540,853 | 7/1996 | Trinh et al. | 510/101 |
| 5,589,162 | 12/1996 | Muraoka et al. | 424/70.12 |

OTHER PUBLICATIONS

Prince, LM, 1975, *The Chemistry and Manufacture of Cosmetics,* vol. III, Second Ed. (Continental Press, Orlando) pp. 25–77.

Kirk–Othmer et al., *Encyclopedia of Chemical Technology,* vol. 8, Third Ed., (Published by John Wiley & Sons) pp. 900–930.

Kirk–Othmer et al., *Encyclopedia of Chemical Technology,* vol. 21, Third Ed., (Published by John Wiley & Sons) pp. 162–180.

*Primary Examiner*—Mark D. Sweet
*Attorney, Agent, or Firm*—Pennie & Edmonds LLP

[57] ABSTRACT

Stable, sprayable compositions suitable for topical application to human skin or hair are provided, along with a method for their preparation. The compositions comprise water-in-oil emulsions and a variety of substantially insoluble dispersed powder. The compositions are useful for applying color to human skin or hair, for protecting human skin from ultraviolet radiation, and for treating human skin or hair with a dermatologically active agent. The compositions have unique suspending power, stability and dispersibility for water-in-oil emulsions.

32 Claims, No Drawings

SPRAYABLE COMPOSITIONS CONTAINING DISPERSED POWDERS AND METHODS FOR USING THE SAME

This is a continuation of application Ser. No. 08/333,707, filed Nov. 3, 1994, now abandoned.

FIELD OF THE INVENTION

The present invention relates to sprayable compositions suitable for topical application to human skin or hair. In particular, the invention relates to stable, sprayable compositions which contain one or more substantially insoluble powders dispersed within water-in-oil emulsions. The sprayable compositions of the invention have excellent suspending power, stability, and dispersibility and are useful to deliver a variety of materials including pharmaceuticals and cosmetics to humans.

The invention also relates to a method for the preparation of such compositions, as well as to the use of such compositions in applying color to human skin or hair, protecting human skin from ultraviolet radiation, treating or protecting human skin or hair with dermatologically active agents, and treating or protecting human skin or hair with pharmacologically active materials.

BACKGROUND OF THE INVENTION

Many cosmetic and pharmaceutical compositions contain substantially insoluble powders dispersed within fluid bases. For example, sunscreen and color cosmetic compositions often contain insoluble inorganic oxides, such as titanium dioxide and iron oxide, dispersed within water-in-oil emulsions. Such compositions should possess significant suspending power, i.e., they should be capable of suspending the dispersed powders, over a wide temperature range and for an extended period of time, without significant precipitation or separation. Additionally, the compositions should deliver the powders to the skin or hair surface in a consistent and reproducible manner. The compositions should be physically and chemically stable, easy to apply, aesthetically pleasing and nonirritating upon application. Similarly, the compositions should be resistant to removal by water or sweat. Cosmetic chemists and formulators have long attempted to develop compositions with these characteristics.

One way in which both suspending power and stability is reported to be achieved in water-in-oil emulsions is by the use of water-swellable clays. See Yoneyama et al., U.S. Pat. No. 5,015,469. Yoneyama et al. is directed, inter alia, to water- and polyhydric alcohol-in-oil type emulsified compositions containing an oil phase containing a polyoxyalkylene modified organopolysiloxane, a water-swellable clay mineral, a quaternary ammonium salt type cationic surfactant and a silicone oil, water, and a polyhydric alcohol, and optionally containing inorganic powders or pigments.

As mentioned above, a highly desirable method for delivering cosmetic compositions to the skin or hair is in the form of a finely dispersed spray. This form of product delivery offers improved product coverage on the skin or hair and easier application to difficult-to-reach areas. Such a spray is said to have good dispersibility and is desirably delivered using a nonaerosol spray pump, which does not require the use of pressurized containers or special aerosolizing gases.

The ability of such pump-driven delivery systems to deliver a product as a finely dispersed spray is critically dependent upon the viscosity of the composition at the exit port of the pump. As the viscosity of the composition decreases, the spray becomes more dispersed yielding a more desirable delivery. Conversely, as the viscosity increases, the spray becomes less dispersed and more stream-like which is less desirable for the application of cosmetics. However, formulators of powder-containing compositions generally rely on the use of higher viscosities to achieve satisfactory suspending power and stability in their formulations. This presents a problem with respect to delivery.

Moreover, it is well-known in the prior art that stable water-in-oil emulsions are generally difficult to prepare at very low viscosities. For example, the compositions disclosed by Yoneyama et al. (U.S. Pat. No. 5,015,469) are described as having a minimum viscosity of about 2500 centipoise, with the viscosity of the disclosed compositions increasing as the weight percent of water-swellable clay mineral is increased.

There is therefore a clear need for stable, water-in-oil compositions that are readily deliverable to the skin or hair as finely dispersed sprays using nonaerosol spray pumps (hereinafter referred to as "sprayable compositions"), while at the same time possessing a high degree of stability and suspending power.

OBJECTS OF THE INVENTION

It is therefore an object of the present invention to provide stable, sprayable compositions suitable for topical application to human skin or hair which contain one or more substantially insoluble powders dispersed within water-in-oil emulsions that have the above-mentioned characteristics. It is a further object of this invention to provide a method for the preparation of such compositions. It is a still further object of this invention to provide methods for using such compositions for applying color to human skin and hair, for protecting human skin from ultraviolet radiation, for treating or protecting human skin or hair with dermatologically active agents, and for treating or protecting human skin with pharmacologically active materials.

SUMMARY OF THE INVENTION

It has now been surprisingly and unexpectedly discovered that sprayable compositions containing one or more substantially insoluble powders dispersed within water-in-oil emulsions and having the above-mentioned characteristics is provided by incorporating into the compositions effective amounts of both electrolytes and oil-swellable organoclays. It has further been discovered that such compositions are surprisingly and unexpectedly shear sensitive, such that the shear imposed on the compositions as they are forced through the orifice of a high shear spray device causes a dramatic and immediate reduction in viscosity, allowing the compositions, with high suspending power, to exit the pump in the form of a finely dispersed spray. One such high shear spray device, the Precision AP1A Spray Pump®, is available commercially from Precision Valve, Inc., Yonkers, N.Y. Other such devices are known to those skilled in the art.

In accordance with the present invention there are provided stable, sprayable compositions suitable for topical application to human skin or hair, which comprise:

(a) from about 20 to about 80 percent of an oil component;

(b) from about 2 to about 12 percent of a water-in-oil emulsifier dispersed within the oil component;

(c) from about 2 to about 20 percent of an organoclay component dispersed within the oil component, wherein the organoclay component comprises from about 5 to about 15 percent of an organoclay, from about 75 to about 95 percent of a nonpolar carrier, and from about 1 to about 10 percent of a polar swelling agent;
(d) from about 1 to about 12 percent of a substantially insoluble powder dispersed within the oil component; and
(e) from about 5 to about 50 percent of an aqueous component emulsified within the oil component to form a water-in-oil emulsion, wherein the aqueous component comprises from about 0.01 to about 2.00 percent of an electrolyte; preferably about 0.05 to about 0.75 percent. These compositions have unique suspending power, stability and dispersibility which was not previously possible with known water-in-oil emulsions The present invention also relates to a method for preparing such compositions, the method comprising:
(a) providing an oil component comprising a water-in-oil emulsifier;
(b) mixing an organoclay component comprising an organoclay, a nonpolar carrier, and a polar swelling agent with the oil component;
(c) mixing a substantially insoluble powder with the oil component; and
(d) blending an aqueous component with the oil component to form a water-in-oil emulsion, the amounts of materials being adjusted such that the resulting composition comprises from about 20 to about 80 percent of the oil component, from about 2 to about 12 percent of the water-in-oil emulsifier, from about 0.1 to about 3 percent of the organoclay, from about 1.5 to about 19 percent of the nonpolar carrier, from about 0.02 to about 2 percent of the polar swelling agent, from about 1 to about 12 percent of the substantially insoluble powder, from about 5 to about 50 percent of the aqueous component, and from about 0.01 to about 2.00 percent of the electrolyte; preferably about 0.05 to about 0.75 percent; and most preferably about 0.2 to about 0.75 percent.

The compositions of this invention are water-in-oil emulsions which are chemically inert and stable against precipitation during extended storage, over a wide temperature range. They are aesthetically pleasing and nonirritating upon application to the skin or hair, resistant to removal by water or sweating, and offer good coverage upon application. The compositions are particularly useful for the delivery of sunscreens, colorants, and pharmacologically active materials, specifically dermatologically active materials, to the skin or hair of humans as well as animals.

DETAILED DESCRIPTION OF THE INVENTION

As mentioned hereinabove, the present invention provides stable, sprayable compositions suitable for topical application to human skin or hair, which comprise:
(a) from about 20 to about 80 percent of an oil component;
(b) from about 2 to about 12 percent of a water-in-oil emulsifier dispersed within the oil component;
(c) from about 2 to about 20 percent of an organoclay component dispersed within the oil component, wherein the organoclay component comprises from about 5 to about 15 percent of an organoclay, from about 75 to about 95 percent of a nonpolar carrier, and from about 1 to about 10 percent of a polar swelling agent;
(d) from about 1 to about 12 percent of a substantially insoluble powder dispersed within the oil component; and
(e) from about 5 to about 50 percent of an aqueous component emulsified within the oil component to form a water-in-oil emulsion, wherein the aqueous component comprises from about 0.01 to about 2.00 percent of an electrolyte; preferably about 0.05 to about 0.75 percent; and most preferably about 0.2 to about 0.75 percent. It should be noted that all weight percents used herein are based on weight percents.

These sprayable compositions have unique suspending power, stability and dispersibility, e.g., the spray delivered is a finely dispersed spray being less streamlike and more mistlike. The characteristics of the compositions enable one to suspend large quantities of powder or powders in the compositions (suspending power) without separation or precipitation of the powder even over long storage times (stability). Further, the compositions enable the product user to achieve excellent distribution of the substantially insoluble powders without the need for vigorous shaking or agitation of the compositions.

The compositions of the present invention are also unexpectedly shear sensitive. As a result, at a standing state the compositions have a high viscosity and can suspend significant amounts of material. In contrast, upon delivery the compositions have a significantly lower viscosity due to the shear force imposed on them as they exit the pump or spray device. This allows for a surprising combination of high suspending power in the bottle and greater dispersibility upon delivery. These characteristics are greatly desirable for water-in-oil emulsions like the present compositions, particularly for the delivery of pharmaceuticals or cosmetics in water-in-oil emulsions.

Each of the components of the compositions of the invention is discussed in greater detail hereinbelow.

1. The Oil Component

The compositions described herein comprise from about 20 to about 80 percent, preferably from about 30 to about 60 percent, of an oil component. The term "oil component" for purposes of this invention refers to any pharmaceutically or cosmetically acceptable material which is substantially insoluble in water. "Pharmaceutically or cosmetically acceptable" as used herein refers to materials that are not known to be harmful to humans. These materials can be found for example in the CTFA International Dictionary of Cosmetic Ingredients as well as the U.S. Pharmacopeia or equivalent sources. The oil components can function in the compositions of the invention as skin and hair conditioning agents, for example as emollients and occlusive agents. Emollients help maintain the softness, smoothness and pliability of skin and hair by remaining on the skin or hair surface and acting as lubricants. Occlusive agents act to increase the water content of skin and hair by minimizing the evaporative loss of water from skin and hair surfaces.

Suitable oil components include, but are not limited to, natural oils, such as coconut oil; hydrocarbons, such as mineral oil and hydrogenated polyisobutene; fatty alcohols, such as octyldodecanol; esters, such as C12–15 alkyl benzoate; diesters, such as propylene glycol dipelargonate; triesters, such as glyceryl trioctanoate; sterol derivatives, such as lanolin; animal waxes, such as beeswax; plant waxes, such as carnauba; mineral waxes, such as ozokerite; petroleum waxes, such as paraffin wax; synthetic waxes, such as polyethylene; and mixtures thereof.

Suitable oil components may also be silicones including, but not limited to, volatile silicones such as cyclomethicone; polymeric silicones such as dimethicone; alkylated derivatives of polymeric silicones, such as cetyl dimethicone and lauryl trimethicone; hydroxylated derivatives of polymeric silicones, such as dimethiconol; and mixtures thereof.

In a preferred embodiment of this invention the oil component comprises a mixture of hydrocarbons and silicones, especially a mixture of hydrocarbons, volatile silicones, and alkylated derivatives of polymeric silicones, most especially a mixture of hydrogenated polyisobutene, cyclomethicone, and cetyl dimethicone. The volatile silicone oil is preferably a low molecular weight silicone. Representative volatile silicone substances include cyclomethicone and lower molecular weight dimethicones or mixtures thereof. Particularly preferred as volatile silicone oils are methylated cyclic organpolysiloxanes, having ring sizes of 4 to 12 such as octamethylcyclotetrasiloxane, an eight membered ring compound formed from four Si—$[CH_3]_2$—O groups and decamethycyclopentasiloxane, a ten membered ring formed from five Si—$[CH_3]_2$—O groups. For purposes of this invention the terms "silicone component" and "oil component" are considered synonymous when applied to compositions in which the oil component consists predominantly or essentially of silicones. Similarly, the terms "water-in-silicone emulsion" and "water-in-oil emulsion" are considered synonymous when applied to such compositions.

2. The Water-In-Oil Emulsifier

The compositions described herein additionally comprise from about 2 to about 12 percent, preferably from about 5 to about 10 percent, of a water-in-oil emulsifier. The term "water-in-oil emulsifier" for purposes of this invention refers to any cosmetically acceptable emulsifier having a hydrophilic-lipophilic balance (HLB) of no greater than 6, preferably from about 2 to about 4. (For an explanation of HLB, see L. M. Prince, in M. G. DeNavarre, "The Chemistry and Manufacture of Cosmetics," Volume III, Second Ed. (Continental Press, Orlando, 1975), pp. 25–37)). Such emulsifiers serve to reduce the interfacial tension between the oil and aqueous components of the compositions of the invention. They may additionally act as cleansing agents, foam boosters and suspending agents, and help to maintain the dispersion of the aqueous component within the oil component for extended periods of time.

Suitable water-in-oil emulsifiers include, but are not limited to, sorbitan derivatives such as sorbitan laurate and sorbitan palmitate; alkoxylated alcohols such as laureth-4; hydroxylated derivatives of polymeric silicones, such as dimethicone copolyol; alkylated derivatives of hydroxylated polymeric silicones, such as cetyl dimethicone copolyol; glyceryl esters such as polyglyceryl-4 isostearate; and mixtures thereof, especially mixtures of hydroxylated derivatives of polymeric silicones, alkylated derivatives of hydroxylated polymeric silicones and glyceryl esters, most especially mixtures of dimethicone copolyol, cetyl dimethicone copolyol and polyglyceryl-4 isostearate. For purposes of this invention the terms "water-in-silicone emulsifier" and "water-in-oil emulsifier" are considered synonymous when applied to compositions in which the oil component consists predominantly or essentially of silicones.

3. The Organoclay Component

The compositions described herein additionally comprise from about 2 to about 20 percent, preferably from about 5 to about 15 percent, of an organoclay component, wherein the organoclay component comprises from about 5 to about 15 percent of an organoclay, from about 75 to about 95 percent of a nonpolar carrier, and from about 1 to about 10 percent of a polar swelling agent. The term "organoclay" for purposes of the present invention refers to any cosmetically acceptable quaternary ammonium complex which is the reaction product of a hydrated aluminum silicate clay and a quaternary ammonium salt. The term "polar swelling agent" as used herein refers to any cosmetically acceptable material which facilitates the expansion of the organoclay into a three-dimensional network within the oil component. The term "nonpolar carrier" as used herein refers to materials that facilitate the incorporation of the organic clay into the oil component.

As noted hereinabove, the compositions of the present invention possess significant suspending power, i.e., they are capable of suspending the substantially insoluble powders, over a wide temperature range and for an extended period of time, without significant precipitation or separation. Without being limited in any way by theory, it is believed that the organoclay provides suspending power to the compositions by swelling to form a three-dimensional network within the oil component. This network, while stable, can be readily disrupted by subjecting the compositions to high shear, such as by forcing the compositions through the nozzle of a spray device. Disruption of the network leads to a significant and immediate reduction in the viscosity of the compositions such that the compositions become sprayable. Accordingly, it is highly desirable for purposes of the present invention that the organoclay be activated by the polar swelling agent towards formation of a three-dimensional network within the organoclay component prior to the incorporation of the organoclay component into the oil component of the compositions described herein.

Preferred organoclays are those which are the reaction products of bentonite clays and quaternium ammonium salts, hectorite clays and quaternium ammonium salts, or montmorillonite clays and quaternium ammonium salts. Especially preferred are organoclays selected from the group consisting of stearalkonium hectorite, quaternium-18 bentonite, quaternium-18 hectorite, and benzalkonium bentonite. These organoclays are available commercially under the trade names Bentone$^R$ (Rheox, Inc., Hightstown, N.J.) and Claytone$^R$ (Southern Clay Products, Gonzales, Tex.).

Suitable polar swelling agents include, but are not limited to, lower monohydric alcohols such as ethanol and isopropyl alcohol; polar esters such as propylene carbonate; water; and the like.

Suitable nonpolar carriers include, but are not limited to, natural oils, such as castor oil and lanolin oil; hydrocarbons, such as mineral oil, petroleum distillates, and isododecane; esters, such as isopropyl palmitate, isopropyl myristate and C12–C15 alkyl benzoate; diesters, such as propylene glycol dicaprylate; volatile silicones such as cyclomethicone; polymeric silicones such as dimethicone; and the like.

The organoclay component is prepared by combining the organoclay, nonpolar carrier and polar swelling agent in any of the mill-type, homogenizer-type, rotor-stator-type mixers available to the art skilled. Such mixers include, but are not limited to, roller mills, ball mills and colloid mills. Alternatively, commercial preparations comprising organoclays, nonpolar carriers, and polar swelling agents, such as those available under the trade name Bentone Gel$^R$ (Rheox, Inc., Hightstown, N.J.), may be employed as the organoclay component of the present invention.

4. The Substantially Insoluble Powder

The compositions described herein additionally comprise from about 1 to about 12 percent, preferably from about 3 to about 9 percent, of a substantially insoluble powder. The term "substantially insoluble powder", as used herein, is meant to include any cosmetically acceptable, finely divided solid which is substantially insoluble in both the aqueous and oil components of the compositions of the invention. Suitable powders for purposes of the present invention include, but are not limited to, sunscreens; colorants; pharmacologically active, specifically dermatologically active materials; cosmetic additives; and the like.

In a preferred embodiment of the present invention the substantially insoluble powder comprises at least one material which is a sunscreen. The term "sunscreen" as used herein refers to any material which is capable of protecting human skin from ultraviolet radiation having a wavelength of from about 280 to about 400 nm, by effectively absorbing such radiation, and/or reflecting or scattering such radiation away from the surface of human skin.

Suitable sunscreens for purposes of this invention include inorganic sunscreens including, but not limited to, titanium derivatives such as titanium dioxide, especially titanium dioxide having an average particle size of from 10 to 100 nanometers, most especially titanium dioxide having an average particle size of from 10 to 100 nanometers and comprising a hydrophobic coating agent to minimize agglomeration; zinc derivatives such as zinc oxide, especially zinc oxide having an average particle size of from 10 to 100 nanometers; polymeric sunscreens, such as melanin and melanin derivatives; and mixtures thereof. Titanium dioxide having an average particle size of from 10 to 100 nanometers and comprising a hydrophobic coating agent comprising aluminum laurate is especially preferred and is available commercially under the trade name Titanium Dioxide Micro LA-20 (Grant Industries, Elmwood Park, N.J.).

In another embodiment of this invention the substantially insoluble powder comprises at least one material which is a colorant. Suitable colorants include, but are not limited to, metals such as bronze powder; metal oxides such as iron oxide; silicates such as mica; and lakes such as D&C Blue No. 1 Aluminum Lake and D&C Red No. 7 Barium Lake.

In yet another embodiment of this invention the substantially insoluble powder comprises a dermatologically active material. Suitable dermatologically active materials include, but are not limited to, antiperspirant agents, such as aluminum chlorohydrate; antiacne agents, such as sulfur; antidandruff agents such as zinc pyrithione; antifungal agents, such as tolnaftate; antiinflammatory agents, such as hydrocortisone and indomethacin; and the like.

In another embodiment of this invention the powder comprises one or more cosmetic additives which serve to modify the physical and/or aesthetic characteristics of the compositions. Such materials include, but are not limited to, additives for reducing tackiness, such as boron nitride; bulking agents, such as nylon and polyethylene; film forming agents, such as polystyrene; absorbants such as talc; and the like. The specific type and amount of such materials will vary with the desired physical and aesthetic characteristics of the compositions, and is readily determined by the skilled artisan.

5. The Aqueous Component

The compositions described herein additionally comprise from about 5 to about 50 percent, preferably from about 25 to about 35 percent, of an aqueous component. For purposes of this invention the term "aqueous component" refers to any pharmaceutically or cosmetically acceptable material consisting essentially or predominantly of water. The aqueous component of the compositions of the invention serves to increase the water content of the skin and hair surfaces, and to retard moisture loss from such surfaces over time.

The aqueous component optionally contains one or more water-soluble emollients including, but not limited to, lower molecular weight aliphatic diols such as propylene glycol and butylene glycol; polyols such as glycerine and sorbitol; and polyoxyethylene polymers such as polyethylene glycol 200. The specific type and amount of water soluble emollient(s) employed will vary depending on the desired aesthetic characteristics of the composition, and is readily determined by the art skilled.

The aqueous component of the compositions of the present invention also comprises from about 0.01 to about 2.00 percent, especially from about 0.05 to about 0.75, and most especially from about 0.2 to about 0.75 percent, of an electrolyte or combination of electrolytes. Suitable electrolytes for purposes of the invention include, but are not limited to, inorganic electrolytes, organic electrolytes, and polyelectrolytes. The inorganic electrolytes include, but not limited to, alkali metal salts and alkaline earth salts, especially electrolytes selected from the group consisting of sodium chloride, calcium chloride, magnesium chloride, and magnesium sulfate; preferably sodium chloride. Further, the polyelectrolytes used within the invention include, but are not limited to hyaluronic acid and sodium hyaluronate, polymer JR (polyquaternium-10), cationic guar gum, and Xanthan gum.

In a most preferred embodiment of the present invention both inorganic and polyelectrolytes are employed simultaneously within the compositions in varying levels, which are within the levels disclosed above. For example, sodium chloride and sodium hyaluronate; calcium chloride and sodium hyaluronate, or magnesium chloride and calcium hyaluronate can be used in varying levels for a total weight of electrolyte being from about 0.05 to about 0.75.

The compositions of the present invention optionally may contain one or more of the following cosmetically acceptable materials including, but not limited to water soluble colorants (such as FD&C Blue #1); oil soluble colorants (such as D&C Green #6); water soluble sunscreens (such as Eusolex 232); oil soluble sunscreens (such as Octyl Methoxycinnamate); particulate sunscreens (such as Zinc Oxide); antimicrobial agents (such as Benzalkonium Chloride); antioxidants (such as BHT); chelating agents (such as Disodium EDTA); emulsion stabilizers (such as carbomer); preservatives (such as Methyl Paraben); fragrances (such as pinene); flavoring agents (such as sorbitol); humectants (such as glycerine); waterproofing agents (such as PVP/Eicosene Copolymer); water soluble film-formers (such as Hydroxypropyl methylcellulose); oil-soluble film formers (such as Hydrogenated C-9 Resin); cationic polymers (such as polyquaternium 10); anionic polymers (such as xanthan gum); vitamins (such as Tocopherol); and the like.

The present invention also relates to a method for the preparation of stable, sprayable compositions suitable for topical application to skin or hair, the method comprising:

(a) providing an oil component comprising a water-in-oil emulsifier;

(b) mixing an organoclay component comprising an organoclay, a nonpolar carrier, and a polar swelling agent with the oil component;

(c) mixing a substantially insoluble powder with the oil component; and (d) blending an aqueous component with the oil component to form a water-in-oil emulsion, the amounts of materials being adjusted such that the resulting composition comprises from about 20 to about 80 percent of the oil component, from about 2 to about 12 percent of the water-in-oil emulsifier, from about 0.1 to about 3 percent of the organoclay, from about 1.5 to about 19 percent of the nonpolar carrier, from about 0.02 to about 2 percent of the polar swelling agent, from about 1 to about 12 percent of the substantially insoluble powder, from about 5 to about 50 percent of the aqueous component, and from about 0.05 to about 0.75 percent of the electrolyte.

It is to be understood that the method for preparation of the compositions of this invention is not limited in any way by the order of the steps set forth above. It is also to be understood that the term "mixing" as used herein includes, but is not limited to, any of the methods of suspending, dissolving or dispersing known to those skilled in the art. Similarly, the term "mixture" includes, but is not limited to, any suspensions, solutions or dispersions prepared by such methods. It is further to be understood that the terms "blending" and "emulsifying" as used herein refer to any of the methods of high shear mixing known to those skilled in the art. Such methods include, but are not limited to, the use of high shear mixing equipment such as a Greerco[R] colloid mill, a Silverson[R] homogenizer, Medsonics ultrasonic mixer or a Microfluidizer[R]. The following non-limiting examples illustrate various embodiments of the present invention.

Example 1: Sunscreen Composition

| Component | CTFA Name | Approximate Weight Percent |
|---|---|---|
| Phase 1 (Oil) | | |
| Panalane L-14E[1] | Hydrogenated Polyisobutene | 5.000 |
| BHT | BHT | 0.200 |
| Ganex V-216[2] | PVP/Hexadecene Copolymer | 4.000 |
| Dow Corning 344 Fluid[3] | Cyclomethicone | 31.500 |
| Abil WE-09[4] | Cetyl Dimethicone Copolyol/ Polyglyceryl-4 Isostearate/ Hexyl Laurate | 6.000 |
| Dow Corning 3225-C[3] | Cyclomethicone/ Dimethicone Copolyol | 2.000 |
| Phenonip[5] | Phenoxyethanol/Methylparaben/ Ethylparaben/Propylparaben/ Butylparaben | 0.500 |
| Abil Wax 9814[4] | Cetyl Dimethicone | 2.000 |
| Phase 2 (Organoclay) | | |
| Claytone SO[6] | Quaternium-18 Bentonite | 0.800 |
| Dow Corning 344 Fluid[3] | Cyclomethicone | 7.000 |
| Propylene Carbonate | Propylene Carbonate | 0.200 |
| Phase 3 (Powder) | | |
| Titanium Dioxide Micro LA-20[7] | Titanium Dioxide/Lauric Acid/Aluminum Hydroxide | 6.000 |
| Elefac I-205[8] | Octyldodecyl Neopentanoate | 9.000 |
| Phase 4 Fragrance | Fragrance | 0.100 |
| Phase 5 (Aqueous) | | |
| Water | Water | 25.000 |
| Sodium Chloride | Sodium Chloride | 0.500 |
| Phase 6 (Aqueous) | | |
| Sodium Hyaluronate[9] | Sodium Hyaluronate | 0.001 |
| Water | Water | 0.199 |

[1]Amoco Chemical Co., Chicago, IL
[2]International Specialty Products, Wayne, NY
[3]Dow Corning Corp., Mount Olive, NJ
[4]Goldschmidt Chemical Corp., Hopewell, VA
[5]Nipa Laboratories, Inc., Wilmington, DE
[6]Southern Clay Products, Gonzales, TX
[7]Grant Industries Inc., Elmwood Park, NJ
[8]Bernel Chemical Co., Inc., Englewood, NJ
[9]Biomatrix, Inc., Ridgefield, NJ Procedure Phase 1 components are combined and mixed at about 35° C. until the BHT has dissolved. Phases 2 and 3 are each combined and milled in a roller mill, ball mill or colloid mill until smooth pastes are formed. Phases 5 and 6 are each combined and mixed until clear solutions are obtained. Phases 2–6 are sequentially added to phase 1 with mixing, and the resultant emulsion blended until smooth.

Examples 2 and 3 are prepared essentially according to the procedure of Example 1, as follows:

Example 2: Antifungal Composition

| Component | CTFA Name | Approximate Weight Percent |
|---|---|---|
| Phase 1 (Oil) | | |
| Panalahe L-14E | Hydrogenated Polyisobutene | 5.000 |
| BHT | BHT | 0.200 |
| Ganex V-216 | PVP/Hexadecene Copolymer | 4.000 |
| Dow Corning 344 Fluid | Cyclomethicone | 36.500 |
| Abil WE-09 | Cetyl Dimethicone Copolyol/ Polyglyceryl-4 isostearate/ Hexyl Laurate | 6.000 |
| Dow Corning 3225-C | Cyclomethicone/ Dimethicone Copolyol | 2.000 |
| Phenonip | Phenoxyethanol/Methylparaben/ Ethylparaben/Propylparaben/ Butylparaben | 0.500 |
| Abil Wax 9814 | Cetyl Dimethicone | 2.000 |
| Phase 2 (Organoclay) | | |
| Bentone 27 | Stearalkonium Hectorite | 0.800 |
| Dow Corning 344 Fluid | Cyclomethicone | 7.000 |
| Propylene Carbonate | Propylene Carbonate | 0.200 |
| Phase 3 (Powder) | | |
| Tolnaftate USP[1] | Tolnaftate | 1.000 |
| Finsolv TN[2] | C12–15 Alkyl Benzoate | 9.000 |
| Phase 4 Fragrance | Fragrance | 0.100 |
| Phase 5 (Aqueous) | | |
| Water | Water | 25.000 |
| Sodium Chloride | Sodium Chloride | 0.500 |
| Phase 6 (Aqueous) | | |
| Sodium Hyaluronate | Sodium Hyaluronate | 0.001 |
| Water | Water | 0.199 |

[1]Barnet Products Corp., Englewood Cliffs, NJ
[2]Finetex, Inc., Elmwood Park, NJ Example 3: Makeup Composition

| Component | CTFA Name | Approximate Weight Percent |
|---|---|---|
| Phase 1 (Oil) | | |
| Panalane L-14E | Hydrogenated Polyisobutene | 5.000 |
| BHT | BHT | 0.200 |
| Ganex V-216 | PVP/Hexadecene Copolymer | 4.000 |
| Dow Corning 344 Fluid | Cyclomethicone | 35.500 |
| Abil WE-09 | Cetyl Dimethicone Copolyol/ Polyglyceryl-4 Isostearate/ Hexyl Laurate | 6.000 |
| Dow Corning 3225-C | Cyclomethicone/ Dimethicone Copolyol | 2.000 |
| Phenonip | Phenoxyethanol/Methylparaben/ Ethylparaben/Propylparaben/ Butylparaben | 0.500 |
| Abil Wax 9814 | Cetyl Dimethicone | 2.000 |
| Phase 2 (Organoclay) | | |
| Claytone SO | Quaternium-18 Bentonite | 0.800 |
| Dow Corning 344 Fluid | Cyclomethicone | 7.000 |
| Propylene Carbonate | Propylene Carbonate | 0.200 |
| Phase 3 ((Powder) | | |
| Iron Oxide[1] | Iron Oxide | 2.000 |
| Finsolv TN | C12–18 Alkyl Benzoate | 9.000 |
| Phase 4 Fragrance | Fragrance | 0.100 |

-continued

| Component | CTFA Name | Approximate Weight Percent |
|---|---|---|
| Phase 5 (Aqueous) | | |
| Water | Water | 25.000 |
| Sodium Chloride | Sodium Chloride | 0.500 |
| Phase 6 (Aqueous) | | |
| Sodium Hyaluronate | Sodium Hyaluronate | 0.001 |
| Water | Water | 0.199 |

[1]US Cosmetics Corp., Dayville, CT

The present invention also relates to methods of using the compositions of the present invention to treat or to protect the skin or hair of a human e.g., from the undesirable effects of exposure to ultraviolet radiation, or from smoke or other extrinsic factors which damage the skin. The present invention also relates to the use of the compositions of the present invention to treat or protect human skin or hair with colorants e.g., for the application of color to hair, the application of an artificial tan to the skin, or the application of artificial whitening to the skin. These methods comprise the application of an effective amount of the appropriate composition to the skin or hair.

While the present invention has been set forth in terms of specific embodiments thereof, it will be understood that numerous variations are now enabled to those skilled in the art. Accordingly, the invention is to be broadly construed and limited only by the scope of the appended claims.

What is claimed is:

1. A sprayable composition suitable for topical application to human skin or hair which comprises:

(a) from about 20 to about 80 percent of an oil component;

(b) from about 2 to about 12 percent of a water-in-oil emulsifier dispersed within the oil component;

(c) from about 2 to about 20 percent of an organoclay component dispersed within the oil component, wherein the organoclay component comprises from about 5 to about 15 percent of an organoclay, from about 75 to about 95 percent of a nonpolar carrier, and from about 1 to about 10 percent of a polar swelling agent;

(d) from about 1 to about 12 percent of a substantially insoluble powder dispersed within the oil component; and (e) from about 5 to about 50 percent of an aqueous component emulsified within the oil component to form a water-in-oil emulsion, wherein the aqueous component comprises from about 0.01 to about 2.00 percent of an electrolyte, said composition being sprayable via non-aerosol means, and undergoing a reduction in viscosity upon exposure to a shear force exerted by said non-aerosol means.

2. The composition of claim 1, further comprising a waterproofing agent.

3. The composition of claim 1, wherein the oil component comprises a silicone.

4. The composition of claim 3, wherein the silicone is a volatile silicone.

5. The composition of claim 1, wherein the organoclay is the reaction product of a hydrated aluminum silicate clay and a quaternary ammonium salt.

6. The composition of claim 5, wherein the organoclay is selected from the group consisting of quaternium-18 bentonite, quaternium-18-hectorite, benzalkonium bentonite, stearalkonium hectorite, and stearalkonium bentonite or a mixture thereof.

7. The composition of claim 1, wherein the polar swelling agent is selected from the group consisting of lower monohydric alcohols, polar esters, and water or a combination thereof.

8. The composition of claim 1, comprising from about 0.05 to about 0.75 percent of said electrolyte.

9. The composition of claim 8 comprising from about 0.2 to about 0.75 percent of said electrolyte.

10. The composition of claim 1, wherein the electrolyte is an inorganic electrolyte.

11. The composition of claim 10, wherein the electrolyte is selected from the group consisting of alkali metal salts and alkaline earth salts.

12. The composition of claim 11, wherein the electrolyte is selected from the group consisting of sodium chloride, calcium chloride, magnesium chloride and magnesium sulfate.

13. The composition of claim 12, wherein the electrolyte is sodium chloride.

14. The composition of claim 1, wherein the electrolyte is a polyelectrolyte.

15. The composition of claim 1, wherein the electrolyte is a mixture of an inorganic electrolyte and a polyelectrolyte.

16. The composition of claim 14 or 15, wherein the polyelectrolyte is selected from the group consisting of hyaluronic acid, sodium hyaluronate, polyquarternium-10, cationic guar gum and Xanthan gum.

17. The composition claim 1, wherein the powder comprises a sunscreen.

18. The composition of claim 17, wherein the sunscreen is titanium dioxide.

19. The composition of claim 18, wherein the titanium dioxide has an average particle size of from 10 to 100 nanometers, having a hydrophobic coating agent.

20. The composition of claim 1, wherein the powder comprises a colorant.

21. The composition of claim 1, wherein the powder comprises a dermatologically active material.

22. A method for the preparation of a sprayable, low viscosity composition suitable for topical application to skin or hair, the method comprising the steps of:

(a) providing an oil component comprising a water-in-oil emulsifier;

(b) mixing an organoclay component comprising an organoclay, a nonpolar carrier, and a polar swelling agent with the oil component;

(c) mixing a substantially insoluble powder with the oil component; and (d) blending an aqueous component with the oil component to form a water-in-oil emulsion, the amounts of materials being adjusted such that the resulting composition comprises from about 20 to about 80 percent of the oil component, from about 2 to about 12 percent of the water-in-oil emulsifier, from about 0.1 to about 3 percent of the organoclay, from about 1.5 to about 19 percent of the nonpolar carrier, from about 0.02 to about 2 percent of the polar swelling agent, from about 1 to about 12 percent of the substantially insoluble powder, from about 5 to about 50 percent of the aqueous component, and from about 0.01 to about 2.00 percent of the electrolyte, said composition being sprayable via non-aerosol means, and undergoing a reduction in viscosity upon exposure to a shear force exerted by said non-aerosol means.

23. A sprayable composition suitable for protecting human skin from ultraviolet radiation, the composition comprising:

(a) from about 30 to about 60 percent of a silicone component;

(b) from about 5 to about 10 percent of a water-in-silicone emulsifier dispersed within the silicone component;

(c) from about 2 to about 20 percent of an organoclay component dispersed within the silicone component, wherein the organoclay component comprises from about 5 to about 15 percent of an organoclay selected from the group consisting of quaternium-18 bentonite, benzalkonium bentonite, and stearalkonium bentonite, from about 75 to about 95 percent of a nonpolar carrier, and from about 1 to about 10 percent of a polar swelling agent;

(d) from about 3 to about 9 percent of titanium dioxide dispersed within the silicone component; and (e) from about 25 to about 35 percent of an aqueous component emulsified within the silicone component to form a water-in-silicone emulsion, wherein the aqueous component comprises from about 0.01 to about 2.00 percent of an electrolyte, said composition being sprayable via non-aerosol means, and undergoing a reduction in viscosity upon exposure to a shear force exerted by said non-aerosol means.

24. The composition of claim 23 comprising from about 0.05 to about 0.75 percent of an electrolyte.

25. The composition of claim 24 comprising from about 0.2 to about 0.75 percent of an electrolyte.

26. The composition of claim 23 wherein said electrolyte is a mixture of an inorganic electrolyte and a polyelectrolyte.

27. The composition of claim 23, wherein the electrolyte is selected from the group consisting of sodium chloride, magnesium chloride and calcium chloride.

28. A method of applying color to human skin or hair which comprises applying the composition of claims 20 or 23 to the skin or hair.

29. A method of protecting human skin against the effects of ultraviolet radiation which comprises applying the composition of claims 1, 17, 18 or 19 onto the skin.

30. A method of treating human skin or hair with a dermatologically active agent which comprises spraying the composition of claim 20 to the skin or hair.

31. The composition of claim 23 wherein the silicone component is a volatile silicone.

32. The composition of claim 23 further comprising a waterproofing agent.

* * * * *